US009243076B2

(12) United States Patent
Freiss et al.

(10) Patent No.: US 9,243,076 B2
(45) Date of Patent: *Jan. 26, 2016

(54) INCLUSION COMPLEXES CONTAINING PIROXICAM, A CYCLODEXTRIN AND ARGININE

(71) Applicant: PIERRE FABRE MEDICAMENT, Boulogne-Billancourt (FR)

(72) Inventors: Bernard Freiss, Castres (FR); Florence Marciacq, Brens (FR); Hubert Lochard, Albi (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 99 days.

This patent is subject to a terminal disclaimer.

(21) Appl. No.: 13/873,959

(22) Filed: Apr. 30, 2013

(65) Prior Publication Data

US 2013/0316975 A1 Nov. 28, 2013

Related U.S. Application Data

(63) Continuation of application No. 10/594,740, filed as application No. PCT/FR2005/000739 on Mar. 29, 2005, now Pat. No. 8,461,133.

(30) Foreign Application Priority Data

Apr. 1, 2004 (FR) ...................................... 04 03450
Oct. 21, 2004 (FR) ...................................... 04 11201

(51) Int. Cl.
| | | |
|---|---|---|
| *A61K 31/5415* | (2006.01) | |
| *A61K 47/40* | (2006.01) | |
| *C08B 37/16* | (2006.01) | |
| *A61K 47/48* | (2006.01) | |
| *B82Y 5/00* | (2011.01) | |

(52) U.S. Cl.
CPC ......... *C08B 37/0015* (2013.01); *A61K 31/5415* (2013.01); *A61K 47/48969* (2013.01); *B82Y 5/00* (2013.01)

(58) Field of Classification Search
CPC .................... A61K 31/5415; A61K 47/48969
See application file for complete search history.

(56) References Cited

U.S. PATENT DOCUMENTS

| 5,070,081 A | 12/1991 | Majid et al. |
| 5,486,508 A | 1/1996 | Uda et al. |

FOREIGN PATENT DOCUMENTS

| EP | 0 066 458 A1 | 12/1982 |
| EP | 0 153 998 A2 | 9/1985 |
| EP | 0 449 167 A1 | 10/1991 |
| EP | 0 524 632 A1 | 1/1993 |
| EP | 1 018 340 A9 | 7/2000 |
| EP | 0 991 407 B9 | 11/2001 |
| SK | SR 280773 B | 7/2000 |
| WO | WO 99/04765 A2 | 2/1999 |
| WO | WO 02/32462 A1 | 4/2002 |
| WO | WO 02/089851 | 11/2002 |
| WO | WO 03/030867 A2 | 4/2003 |
| WO | WO 03/043604 A | 5/2003 |
| WO | WO 03/105906 A | 12/2003 |
| WO | WO 2004/096284 A | 11/2004 |
| WO | WO 2005/112637 A | 12/2005 |

OTHER PUBLICATIONS

Vikmon et al., J. J. T. Labandeira et al. (eds.), Proceedings of the Ninth International Symposium on Cyclodextrins, 1999, Springer Netherlands, p. 281-284.*
Bersani Amado et al., Gen. Pharmac., 1995, 26(4), p. 809-813.*
Barillaro, V. et al.; Proceeding of 7th Intl. Cyclodextrins Symposium, pp. 414-418 (1994).
Bordner, Jon et al.; Acta Cryst., C40, pp. 989-990 (1984).
Buvari-Barcza et al., J. of Inclusion Phenomena and Macrocyclic Chemistry, vol. 42, pp. 209-212 (2002).
Caira, Mino R. et al.; J. Chem. Soc., Chem. Commun., pp. 1061-1062 (1994).
Definition of "stage", Merriam Webster Online Dictionary, http://www.merriam-webster.com/dictionary, accessed online on Dec. 15, 2008.
Derwent Publications Ltd., London, BG; An 1993-098122XP002375837, Lee S.: process for preparing stabilzed injectable pyroxicam composition & KR 9 206 911 B ((Shin-N) Shin Poong Pharm CO), Aug. 22, 1992.
Escandar, G.M. , Analyst, No. 124, pp. 587-591 (1999).
Fenyvesi et al., Proceedings of the 7th Intl. Cyclodextrins Symposium, pp. 414-418 (1994).
Fenyvesi, E. et al.; Journal of Inclusion Phenomena and Macrocyclic Chemistry, vol. 33, pp. 339-344 (1999).

(Continued)

*Primary Examiner* — Jonathan S Lau
(74) *Attorney, Agent, or Firm* — Birch, Stewart, Kolasch & Birch, LLP

(57) ABSTRACT

The invention relates to a method for preparing a soluble inclusion complex comprising one or several active substances which are hardly soluble in an aqueous medium and are included in one or several host molecules, using the following successive stages: (a) bringing one or several active substances into contact with one or several host molecules; (b) initiating a molecular diffusion stage by bringing a dense pressurized fluid into contact with the mixture obtained in (a) in a static mode in the presence of one or several diffusing agents; (c) recovering the active substance-host molecule molecular complex formed; (d) adding and mixing an interaction agent with the active substance-host molecule molecular complex; (e) recovering the soluble inclusion compound thus formed. The invention also relates to the soluble inclusion compound obtained by the method, particularly a piroxicam-cyclodextrin-arginine compound.

15 Claims, 14 Drawing Sheets

(56) References Cited

OTHER PUBLICATIONS

Galia et al., "Complexation of Phosphine Ligands with Peracetylated β-Cyclodextrin in Supercritical Carbon Dioxide: Spectroscopic Determination of Equilibrium Constants", J. Phys. Chem. B, 2007, vol. 111, pp. 2573-2578.

Hees Van T et al., Journal De Pharmacie De Belgique, Masson Paris, FR, vol. 55, No. 1, Jan. 2000, pp. 30-31.

Hees Van T et al., Journal of Inclusion Phenomena and Macrocyclic Chemistry, Kluwer, Dordrecht, Nl, vol. 44, 2002, pp. 271-274.

Hees Van T et al., Pharmacological Research, Academic Press, London, GB, vol. 16, No. 12, 1999, pp. 1864-1870.

Hong, Seok Cheon et al.; 33(2), 85-89 (2003), Chemical Abstract.

Junco et al., "Optimisation of Supercritical Carbon Dioxide Systems for Complexation of Naproxen: Beta-Cyclodextrin", Journal of Inclusion Phenomena and Macrocyclic Chemistry, 2002, vol. 44. pp. 69-73.

Jung, J. et al.; Journal of Supercritical Fluids, 20, pp. 179-219 (2001).

Kamihira M et al., Journal of Fermentation and Bioengineering, Society of Fermentation Technology, JP, vol. 69, No. 6, 1990, pp. 350-353.

Lieberman et al., Pharmaceutical Dosage Forms—Disperse Systems, 1998, Marcel Dekker, Inc., 2nd ed., pp. 1-46.

Moribe et al., "Solubility-dependent complexation of active pharmaceutical ingredients with trimethyl-β-cyclodextrin under supercritical fluid condition", Journal of Inclusion Phenomena and Macrocyclic Chemistry, 2007, vol. 57, pp. 289-295.

Mura P. et al., International Journal of Pharmaceutics, vol. 260, 2003, pp. 293-302.

Mura, P. et al.; Journal of Inclusion Phenomena and Macrocyclic Chemistry, vol. 39, pp. 131-138 (2001).

Piel, G. et al.; Journal of Pharmaceutical Sciences, vol. 86, No. 4, pp. 475-480 (1997).

Redenti, E. et al.; J. of Pharmaceutical Sciences, vol. 89, pp. 1-8 (2000).

Rodier E. et al., European Journal of Pharmaceutical Science, vol. 26, 2005, pp. 184-193.

Subramaniam, B. et al., Journal of Pharm. Sciences, vol. 86, No. 8, pp. 885-890 (1997).

Vrecer, F. et al., International Journal of Pharmaceutics, 68, pp. 35-41 (1991).

Wiseman, E.H. et al.; Arzneim.-Forsch./Drug.Res. 26, No. 7, pp. 1300-1303 (1976).

\* cited by examiner

INCLUSION COMPLEXES CONTAINING PIROXICAM, A CYCLODEXTRIN AND ARGININE

CROSS REFERENCE TO RELATED APPLICATIONS

This application is a Continuation of co-pending application Ser. No. 10/594,740, filed on Sep. 29, 2006, the entire contents of which are hereby incorporated by reference and for which priority is claimed under 35 U.S.C. §120. Application Ser. No. 10/594,740 is the national phase of PCT International Application No. PCT/FR2005/000739 filed on Mar. 29, 2005 under 35 U.S.C. §371, which claims priority under 35 U.S.C. §119(a) to Patent Application Nos. 0403450 and 0411201 filed in France on Apr. 1, 2004 and Oct. 21, 2004, respectively. The entire contents of each of the above-identified applications are hereby incorporated by reference.

The present invention relates to a process for the preparation of soluble inclusion compounds by the dense pressurized fluids technology, in particular that of $CO_2$.

Numerous active substances, in particular of interest in the pharmaceutical field, exhibit a very low solubility or are insoluble in water and consequently in biological liquids. This implies a low bioavailability of these active substances and a large increase in the doses administered to the patients in order to achieve the therapeutic objective set and thus an increase in the possible side effects related to the medical treatments.

The pharmacokinetic properties of a given substance depend, inter alia, on the affinity of its contact surface for the solvent under consideration, namely water in the case of the pharmaceutical field. The increase in the specific surface of powders makes it possible to improve their rate of dissolution. In point of fact, the bioavailability of active principles can be greatly increased if their rate of dissolution is improved. Consequently, the formation of molecular complexes composed of one or more active substances and of one or more host molecules carefully chosen for its (their) high solubility in biological liquids can thus make it possible to increase dissolution of the active substance or substances in biological liquids.

In the pharmaceutical field, a number of patents and publications exist relating to the formation of cyclodextrin-based complexes in the presence of an agent for interaction with the complex. Nevertheless, the majority of the documents do not provide industrial processes but instead the study of the improvement in the solubility of an active substance/cyclodextrin complex via the agent for interacting with the complex. They relate specifically to a listing of agents for interaction with the complex which are tested for the same active principle, and the analytical results obtained. Furthermore, few documents exist which provide complexing in a supercritical medium.

The documents describing processes for complexing with a cyclodextrin by a supercritical fluid are as follows: With the aim of fixing volatile molecules by inclusion, Kamihira M. et al. (*J. of Fermentation and Bioengineering*, Vol. 69, No. 6, 350-353, 1990) describe a process for the extraction of volatile aromatic compounds and for trapping by inclusion in cyclodextrins. Geraniol and mustard oil are thus extracted by a pressurized fluid and then vaporized in dynamic mode in a second reactor comprising cyclodextrins. The influence of the various parameters is studied by measuring the degree of inclusion of the aromatic compounds in the cyclodextrins. However, the inclusion stage is carried out in dynamic mode and not in static mode. Furthermore, the application claimed by the authors is completely different since it involves fixing volatile molecules by inclusion. Finally, this process is not carried out with supercritical fluids but with pressurized gases.

Van Hees et al. (*Pharmaceutical Research*, Vol. 16, No. 12, 1999) describe, in their publication, a process for the inclusion of commercial piroxicam in β-cyclodextrins with supercritical $CO_2$. As piroxicam is a nonsteroidal anti-inflammatory of low solubility in water, its inclusion in β-cyclodextrins should make it possible to increase its solubility in water. The process consists in placing a mixture of piroxicam and of β-cyclodextrins (molar ratio 1/2.5) in a pressurized autoclave left in static mode. After depressurizing, the mixture obtained is milled and homogenized. The complex is subsequently dried before characterization by:

DSC (differential scanning calorimetry)
Differential solubility technique
Spectroscopic methods.

These analyses make it possible to decide on the degree of complexing of the piroxicam with the β-cyclodextrin. The importance of an agent for interaction with the complex with regard to the dissolution of the complex thus obtained is not mentioned. Furthermore, no diffusion agent is used in the stage of formation of the complex with supercritical $CO_2$ in static mode. Patent Application WO 03/043604 discloses a process for the preparation of molecular complexes of active substances in host molecules. The process employs a stage of molecular diffusion by bringing a dense pressurized fluid into contact in static mode, in the optional presence of a diffusion agent: water.

However, this stage is followed by an obligatory stage of washing with supercritical $CO_2$. Furthermore, no agent for interaction with the complex is used.

Various documents form part of the improvement in the solubility of an active substance by addition of an agent for interaction with the complex (Redenti E. et al, *J. of Pharmaceutical Sciences*, Vol. 89, 1-8, 2000). The solubility of the active substance alone, or the active substance in the presence of the agent for interaction with the complex, of the active substance/cyclodextrin binary complex and finally of the active substance/cyclodextrin/agent for interaction with the complex ternary complex are studied. However, none of the processes described uses supercritical $CO_2$ or in particular a stage of molecular diffusion in static mode using a diffusion agent.

Thus, Buvári-Barcza et al. (*J. of Inclusion Phenomena and Macrocyclic Chemistry*, Vol. 42, 209-212, 2002) study the solubility of benzoic acid/β-cyclodextrin and benzene/β-cyclodextrin complexes in the presence of acetic acid. The solubility of the benzene/β-cyclodextrin complex is independent of the concentration of acetic acid whereas that of the benzoic acid/β-cyclodextrin complex increases with the concentration of acetic acid. The interpretation of the authors is as follows: in the molecule/β-cyclodextrin/acetic acid ternary complex, the potential hydrogen bonds between the molecule and the interior cavity of the cyclodextrin promote other interactions external to the cyclodextrin.

Likewise, Mura et al. (*J. of Inclusion Phenomena and Macrocyclic Chemistry*, Vol. 39, 131-138, 2001) measure the solubility of econazole in the presence of cyclodextrins (α-, β-, γ-, hydroxypropyl-β-cyclodextrins) and of hydroxy acids (tartaric, citric, gluconic, malic and lactic acids). The ternary complexes are prepared by physical mixing or milling of the 3 compounds, coevaporation or lyophilization of a solution comprising the 3 compounds. The formation of a ternary complex is monitored by DSC. Only lyophilization makes it possible to obtain a DSC profile no longer exhibiting the peak for the melting of econazole.

The authors conclude that a synergistic effect is observed in the ternary complex, since the solubilities observed are up to 20 times greater than that of an econazole/cyclodextrin binary complex.

The same authors (*Int. J. of Pharmaceutics*, Vol. 260, 293-302, 2003) have also studied ternary complexes of naproxen/hydroxypropyl-β-cyclodextrin/amino acid type. The complexes mentioned are prepared either by co-milling or by co-evaporation of a water-ethanol solution comprising the 3 compounds.

Piel et al. (*J. of Pharmaceutical Sciences*, Vol. 86-4, 475-480, 1997) present a study of solubility of a nimesulide/L-lysine/β- or γ-cyclodextrin complex obtained by spray drying or evaporation. The solubility of the ternary complex is, depending on the pH of the solution, up to 3600 times greater than that of nimesulide alone. Here again, the authors speak of a synergistic effect of the cyclodextrin and of the L-lysine.

Fenivesy et al. (*Proceedings of the 7th International Cyclodextrins Symposium*, 414-418, 1994) are concerned with the complexing of the active substances terfenadine, domperidone and astemizole with hydroxypropyl-β-cyclodextrin in the presence of hydroxy acids.

Two patents (EP 0 991 407 and EP 1 018 340) disclose the preparation of active substances/agent for interaction with the complex/cyclodextrin ternary complexes. The processes employed are kneading, spray drying, evaporation or lyophilization. The process consists either in preparing the complex of the salt of the active substance or in bringing the 3 compounds into contact simultaneously during the process.

A patent (EP 0 153 998 A2), filed by Chiesi et al., discloses the preparation of complexes of piroxicam and of β-cyclodextrin in the presence in particular of an ammoniacal solution. However, the process used is not carried out with supercritical $CO_2$.

The only two documents relating to the preparation of a complex with supercritical $CO_2$ in the presence of an agent for interaction with the complex are as follows:

By following the same method as that described above (*Pharmaceutical Research*, Vol. 16, No. 12, 1999), Van Hees et al. (*Journal of Inclusion Phenomena and Macrocyclic Chemistry*, No. 44, pp 271-274, 2002) describe the use of an agent for interaction with the complex, L-lysine or trometamol, in the preparation of a piroxicam/β-cyclodextrin complex with supercritical $CO_2$.

The use of L-lysine or of trometamol allows them both to increase the degree of inclusion of the piroxicam in the β-cyclodextrin and to improve the dissolution of the complex formed.

Characterization is carried out by:
DSC (differential scanning calorimetry)
Differential solubility technique
Kinetics of dissolution in a buffered medium However, no diffusion agent is used during this stage. V. Barillaro et al. (Proceeding of the 6th International Symposium on Supercritical Fluids, Versailles, pp 1897-1902, 2003) focused more on the improvement which might be contributed by the addition of an acidic agent for interaction with the complex in increasing the degree of inclusion of miconazole in cyclodextrins. Various agents for interaction with the complex (malic acid, maleic acid, fumaric acid, citric acid) and various cyclodextrins (β-cyclodextrin, HP-β-cyclodextrin, γ-cyclodextrin, HP-γ-cyclodextrin) were used.

However, the inclusion stage is carried out in dynamic mode and not in static mode.

In the two documents mentioned above, it is thus important to know that the complexing with supercritical fluids is carried out on the active substance/agent for interaction with the complex/cyclodextrin ternary mixture and that, furthermore, the agent for interacting with the complex is not arginine.

The piroxicam molecule, represented below, has an enol functional group and a pyridine ring which may or may not be salified according to the pH value of the dissolution medium.

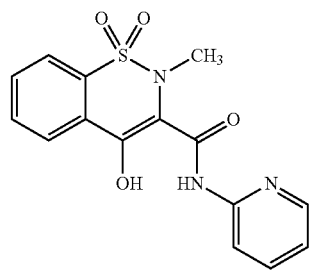 [SMILES: CN1C(C(=O)Nc2ccccn2)=C(O)c2ccccc2S1(=O)=O]

Wiseman et al. (*Arzneim.-Forsch./Drug Res.*, 26 (7), 1976, 1300-1303) have determined, in a 2:1 (v/v) dioxane:water mixture, the pKa value of the enol functional group (pKa~2) and of the pyridine ring (pKa~6.3).

According to the pH value of the dissolution medium, the piroxicam (PX) molecule will thus exist in various forms, namely:

pH<2
the pyridine ring is protonated to give a pyridinium ion ($NY^+$)
the enol functional group is not ionized (—OH)

2<pH<7
the pyridine ring is protonated ($NH^+$)
the enol functional group is ionized to give enolate ($O^-$).

This is the zwitterionic structure of piroxicam. In terms of molecular conformation, the zwitterionic structure is planar. This flatness results from intramolecular hydrogen bonds between the enolate anion and the amide group, on the one hand, and then the carbonyl functional group and the pyridinium cation, on the other hand.

pH>7
the enol functional group is ionized ($O^-$)
the pyridine ring is not protonated (N).

The inventors have discovered, surprisingly, that the separation of the stages of complexing and of addition of the agent for interaction with the complex makes it possible to substantially improve the physicochemical properties of the complex thus obtained. Furthermore, they have also noticed that the use of arginine as agent for interaction with the complex when the active substance is piroxicam makes it possible to obtain complexes having the most advantageous properties.

The object is to improve the in vivo dissolution of a water-insoluble active substance, this being achieved by including the active substance in a soluble porous support and by then modifying the physicochemical properties of the system thus formed.

The present invention thus relates to a process for the preparation of a soluble inclusion compound comprising one or more active substances included in one or more host molecules, the active substance or substances not being very soluble in an aqueous medium, characterized in that it comprises the following successive stages:

a. bringing one or more active substances into contact with one or more host molecules,
b. carrying out a stage of molecular diffusion by bringing a dense pressurized fluid into contact, in static mode, with the mixture obtained in stage (a) in the presence of one or more diffusion agents,
c. recovering the active substance/host molecule molecular complex thus formed,
d. carrying out a stage which consists in adding to and mixing with the active substance/host molecule molecular complex an agent for interaction with the complex,
e. recovering the soluble inclusion compound thus formed.

In the process according to the present invention, there is no stage of washing with supercritical $CO_2$ between stages (c) and (d).

In another advantageous embodiment, stage (e) is followed by a stage (f) of drying the soluble interaction compound, advantageously between 60° C. and 80° C. and advantageously overnight.

The process according to the present invention is thus composed of the linking of two phases, which are:
  the formation of an inclusion complex between an active substance and a host molecule in a supercritical medium (stages (a), (b) and (c))
  the noncovalent "fixing" of an agent for interaction with the complex to the complex obtained, in order in particular to improve its physicochemical properties (stages (d) and (e)).

The invention thus discloses a five-stage process.
  the first three "maturing" stages consist essentially of a phase of molecular diffusion in a dense pressurized medium, and in particular supercritical medium, which makes it possible to include active substances in host molecules, in particular cyclodextrins. The object desired during this diffusion phase is to form inclusion complexes between active substances and the host molecule.

The term "inclusion complex" or "molecular complex" is understood to mean, within the meaning of the present invention, any complex combining in a noncovalent fashion the active substance and the host molecule. Advantageously, it is the complex resulting from stage (b) of the process according to the present invention. The term "soluble inclusion compound" is understood to mean, within the meaning of the present invention, any entity formed by the combination of the agent for interaction with the complex, on the one hand, and the molecular complex, on the other hand. Advantageously, it is the final product obtained by the process according to the present invention.

The term "agent for interaction with the complex" is understood to mean, within the meaning of the present invention, any organic or inorganic agent which improves the physicochemical properties, in particular the properties of dissolution in an aqueous medium, of the molecular complex by interactions without covalent bonds with the active substance included in the host molecule or directly with the molecular complex. Advantageously, the agent for interaction with the complex is a surfactant, for example sodium lauryl sulfate or Tween, an acid or a base. Advantageously, it is an acid or a base. The choice of an acidic or basic agent will depend on the acidic or basic nature of the active substance. Thus, preferably, an acidic agent will be used with a molecular complex comprising a basic active substance and a basic agent with a molecular complex comprising an acidic active substance.

Advantageously, the agent for interaction with the complex is chosen from an amino acid, a carboxylic acid, an acetate, a carboxylate, an amine or aqueous ammonia, advantageously in the form of a 28% ammoniacal solution. More advantageously still, it is chosen from acetic acid, tartaric acid, citric acid, gluconic acid, malic acid, lactic acid, maleic acid, fumaric acid, L-lysine, L-valine, L-isoleucine, L-arginine or aqueous ammonia. More advantageously still, it is aqueous ammonia.

The term "dense pressurized fluid" is understood to mean, within the meaning of the present invention, any fluid used at a temperature or a pressure greater than their critical value. Advantageously, it is pure $CO_2$ or $CO_2$ in a mixture with an organic solvent conventionally used by a person skilled in the art.

The term "active substance which is not very soluble in an aqueous medium" is understood to mean, within the meaning of the present invention, any active substance which is insoluble or not very soluble in an aqueous medium and which has in particular a solubility of less than at least 20 µg/ml. In particular, it can be a pharmaceutical active principle (mention may be made, by way of examples, of analgesics, antipyretics, aspirin and its derivatives, antibiotics, anti-inflammatories, antiulceratives, antihypertensives, neuroleptics, antidepressants, oligonucleotides exhibiting a therapeutic activity, peptides exhibiting a therapeutic activity and proteins exhibiting a therapeutic activity), a cosmetic active principle or a nutraceutic active principle. Advantageously, it is an active substance chosen from the group consisting of anilide derivatives, epipodophyllotoxin derivatives, minoxidil, piroxicam, valeric acid, octanoic acid, lauric acid, stearic acid, tiaprofenic acid, omeprazole, econazole, miconazole, ketoconazole, astemizole, cyclobenzaprine, nimesulide, ibuprofen, terfenadine, domperidone, naproxen and eflucimibe; advantageously, it is piroxicam.

The term "host molecule" is understood to mean, within the meaning of the present invention, any substance capable of capturing active substances. Advantageously, the host molecule is chosen from the group consisting of polysaccharides and saccharides, in particular cyclodextrins and their mixture. Advantageously, it is β-cyclodextrin, methyl-β-cyclodextrin, γ-cyclodextrin or hydroxypropyl-β-cyclodextrin. Advantageously, it is β-cyclodextrin.

Cyclodextrins are "cage" molecules as they comprise, within their structure, a relatively rigid and hydrophobic cavity which allows them to confine or encapsulate other molecules. The complexing phenomenon is the consequence of a multitude of interactions (substrate/solvent, solvent/solvent and cyclodextrin/solvent) which result in the more stable thermodynamic state:
(1) Van der Waals' interactions;
(2) hydrophobic interactions;
(3) hydrogen bonds;
(4) the release of water molecules with a high energy during the substitution by the guest molecule;
(5) the release of the strain energy within the cyclodextrin molecule during the formation of the complex.

Advantageously, the soluble inclusion compound consists of the combination of piroxicam, of a cyclodextrin and of arginine, advantageously L-arginine.

The term "diffusion agent" is understood to mean, within the meaning of the present invention, any solvent which promotes an interaction of the active substance with the host molecule.

Advantageously, this diffusion agent is chosen from the group consisting of alcohols, ketones, ethers, esters and water, with or without surfactant, and their mixtures. More advantageously still, it is water.

The term "static mode" is understood to mean, within the meaning of the present invention, a reaction or a process in which all the reactants are brought together simultaneously and where the reaction is allowed to take place. For example, in stage (b) of the present invention, the active substance(s), water and supercritical $CO_2$ are placed in an autoclave and reaction is allowed to take place for several hours. The weight of product does not change during reaction. Conversely, in dynamic mode, the reactants are introduced as the reaction or manufacture progresses. Often, in the case of a dynamic mode, circulation of a fluid or stirring is involved. The weight of product changes during the manufacture.

During stage (a), the active substance and the host molecule are introduced in solid or liquid form into a receptacle into which are injected, during stage (b), the dense pressurized fluid and the diffusion agent in carefully chosen proportions. The pressure and temperature conditions and the duration of the treatment are defined by any appropriate method according to the nature of the active substance or substances and of the host molecule or molecules. Advantageously, stage (b) of molecular diffusion of the process according to the present invention is carried out with stirring.

The diffusion agent can be added continuously or portionwise in an amount of between 1 and 50% by weight, preferably between 10 and 25% by weight.

The active substance/host molecule/agent for interaction with the complex molar ratio can be chosen so as to ensure the best inclusion of the active substance in the host molecule. Thus, advantageously, the active substance/host molecule molar ratio is between 1/1 and 1/10, advantageously between 1/1 and 1/5, advantageously between 1/2 and 1/2.5, more advantageously still 1/2.5. Likewise, the active substance/agent for interaction with the complex molar ratio is advantageously between 1/1 and 1/3, advantageously 1/1, more advantageously 1/1.2. The time necessary for the molecular diffusion of stage (b) is determined by any appropriate method. This step (b) can be repeated as often as desired in order to obtain a satisfactory rate of dissolution. Advantageously, stage (b) lasts between approximately 1 and 16 hours.

The pressure and temperature conditions of stage (b) are chosen so as to promote molecular diffusion. Advantageously, the pressure of the supercritical fluid is between 0.5 MPa and 50 MPa and the temperature between 0 and 200° C.

Advantageously, stage (b) of the process according to the present invention is carried out in a closed reactor, in particular an autoclave.

The process can be carried out batchwise or continuously. Advantageously, the process according to the present invention is carried out batchwise. Advantageously, stage (b) of the process according to the present invention is carried out in a closed, optionally stirred, reactor fed with the dense fluid and the solution of active substance, if appropriate, continuously.

The final two stages ((d) and (e)) consist in adding to and mixing with the active substance/host molecule complex an agent for interaction with the complex. This agent for interaction with the complex interacts according to two plausible hypotheses: strong interactions with the active substance included in the host molecule during the preceding stages and/or strong interactions with the complex formed previously.

This makes it possible to improve mainly the properties of dissolution of the complex in biological liquids and in particular water and/or optionally to increase the degree of inclusion of the active substance in the host molecule.

The improvement in the physicochemical properties, in particular in terms of dissolution, of the system formed can result from a noncovalent interaction of the agent for interaction with the complex with the active substance, the host molecule or both (complexing, salification, and the like)
a local variation in the pH of the dissolution medium
a production of a system exhibiting a eutectic
a modification of the interface between the system and its dissolution medium (surfactant effect, particle size change).

Advantageously, stage (d) of the process is carried out in a semisolid medium, the complex not being dissolved in an aqueous medium before the addition of the agent for interaction with the complex. This agent will thus simply moisten the complex or form a paste with the complex. Advantageously, stage (d) is carried out with stirring.

The present invention also relates to a soluble inclusion compound comprising one or more active substances included in one or more host molecules, the active substance or substances not being very soluble in an aqueous medium, and an agent for interaction with the complex obtainable by the process according to the present invention.

Advantageously, the degree of inclusion of the active substance in the soluble inclusion compound according to the present invention is greater than 95%, calculated by DSC analysis as described below, advantageously greater than 98%, advantageously approximately 99%.

Advantageously, the solubility of the active principle when it is found in the form of the complex according to the present invention is greater than 2.5 g/l, advantageously at least equal to 3 g/l. Advantageously, the degree of dissolution of the active substance present in a 4 g/l solution in water, measured at 38° C. after stirring for between 5 and 120 minutes, is greater than 63%, advantageously at least equal to 75%. Advantageously, the active substance is piroxicam and the solubility and the degree of dissolution are measured at pH=6.3.

Advantageously, the host molecule is cyclodextrin and the active substance is piroxicam.

Advantageously, piroxicam is present in the complex according to the present invention with a zwitterionic structure.

In the context of the present invention, the term "degree of dissolution" is understood to mean the percentage of piroxicam dissolved after stirring a mixture of water and of piroxicam at 37° C. for 5 to 120 minutes. A 4 g/l mixture of piroxicam in water will generally be used to measure this degree. This dissolution can be measured by a dissolution test as indicated below (dissolution test for piroxicam).

The present invention additionally relates to a complex comprising piroxicam, a cyclodextrin and arginine, characterized in that the degree of dissolution of the piroxicam present in a 4 g/l solution in water, measured at 37° C. after stirring for between 5 and 120 minutes, is greater than 90%, advantageously greater than 95%, advantageously equal to 99%.

The term "cyclodextrins" is understood to mean, within the meaning of the present invention, cyclodextrins, modified cyclodextrins and their mixtures. Advantageously, the cyclodextrin is β-cyclodextrin, methyl-β-cyclodextrin, γ-cyclodextrin or hydroxypropyl-β-cyclodextrin. Advantageously, it is β-cyclodextrin.

Advantageously, the piroxicam/cyclodextrin/arginine complex according to the present invention exhibits good crystallinity. Advantageously, this complex exhibits less than 40% by weight of amorphous phase, more advantageously still less than 30% by weight of amorphous phase, advantageously an amount of amorphous phase of less than or equal to 20% by weight.

Advantageously, the degree of inclusion of piroxicam in the piroxicam/cyclodextrin/arginine complex according to the present invention, measured by differential scanning calorimetry as described below, is greater than 98%, advantageously greater than 99%, advantageously approximately 100%.

Advantageously, piroxicam is present in the complex according to the present invention with a zwitterionic structure.

The piroxicam/cyclodextrin/arginine complexes according to the present invention are obtainable by the process according to the present invention as described above. However, they are also obtainable by the process below.

Thus, a process for the preparation of a piroxicam/cyclodextrin/arginine complex according to the present invention comprises the following successive stages:
(1) bringing piroxicam into contact with a cyclodextrin and arginine,
(2) carrying out a stage of molecular diffusion by bringing a dense pressurized fluid into contact, in static mode, with the mixture obtained in stage (1) in the presence of one or more diffusion agents,
(3) recovering the piroxicam/cyclodextrin/arginine complex thus formed.

This process makes it possible, in the case of piroxicam/cyclodextrin/arginine complexes, to obtain complexes having specific properties.

Stage (2) of molecular diffusion in static mode, referred to as maturing stage, consists essentially of a phase of molecular diffusion in a dense pressurized medium, and in particular a supercritical medium, which makes it possible to include piroxicam in the cyclodextrins. The object desired during this diffusion phase is to form inclusion complexes between piroxicam, the cyclodextrin and arginine.

The complex thus formed combines piroxicam, the cyclodextrin and arginine in a noncovalent manner. Arginine, which acts as interaction agent, interacts according to two plausible hypotheses: strong interactions with piroxicam included in the cyclodextrin and/or strong interactions with the complex formed.

The presence of arginine makes it possible to improve mainly the properties of dissolution of the complex in biological liquids and in particular water.

The improvement in the physicochemical properties, in particular in terms of dissolution, of the system formed can result from
a noncovalent interaction of arginine with piroxicam, the cyclodextrin or both (complexing, salification, and the like)
a local variation in the pH of the dissolution medium
a production of a system exhibiting a eutectic
a modification of the interface between the system and its dissolution medium (surfactant effect, particle size change).

The term "dense pressurized fluid" is understood to mean, within the meaning of the present invention, any fluid used at a temperature or a pressure greater than their critical value. Advantageously, it is pure $CO_2$ or $CO_2$ as a mixture with an organic solvent conventionally used by a person skilled in the art.

The term "diffusion agent" is understood to mean, within the meaning of the present invention, any solvent which promotes an interaction of piroxicam and the cyclodextrins.

Advantageously, this diffusion agent is chosen from the group consisting of alcohols, ketones, ethers, esters and water, with or without surfactant, and their mixtures. More advantageously still, it is water.

The term "static mode" is understood to mean, within the meaning of the present invention, a reaction or a process in which all the reactants are brought together simultaneously and where the reaction is allowed to take place. For example, in stage (2) of the present invention, piroxicam, the water, arginine and supercritical $CO_2$ are placed in an autoclave and reaction is allowed to take place for several hours. The weight of product does not change during reaction. Conversely, in dynamic mode, the reactants are introduced as the reaction or manufacture progresses. Often, in the case of a dynamic mode, circulation of a fluid is involved. The weight of product changes during the manufacture.

Advantageously, stage (2) of molecular diffusion of the process according to the present invention is carried out with stirring.

In a specific embodiment of the invention, during stage (1), piroxicam, arginine and the cyclodextrins are introduced in the solid or liquid form into a receptacle into which are injected the dense pressurized fluid and the diffusion agent in carefully chosen proportions. The pressure and temperature conditions and the duration of the treatment are defined by any appropriate method.

The piroxicam/cyclodextrin/arginine molar ratio can be chosen so as to provide the best inclusion of piroxicam in the cyclodextrins. Thus, advantageously, the piroxicam/cyclodextrin molar ratio is between 1/1 and 1/10, advantageously between 1/1 and 1/5, advantageously between 1/2 and 1/2.5, more advantageously still 1/2.5. Likewise, the piroxicam/arginine molar ratio is advantageously between 1/1 and 1/3, advantageously 1/1, more advantageously 1/1.2.

The diffusion agent can be added continuously or portionwise in an amount of between 1 and 50% by weight with respect to the total weight of the mixture, advantageously between 20 and 25% by weight with respect to the total weight of the mixture.

The time necessary for the molecular diffusion of stage (2) is determined by any appropriate method. This stage (2) can be repeated as often as desired in order to obtain a satisfactory rate of dissolution. Advantageously, stage (2) lasts between approximately 2 and 16 hours, advantageously 1 hour.

The pressure and temperature conditions of stage (2) are chosen so as to promote molecular diffusion. Advantageously, the pressure of the supercritical fluid is between 5 MPa and 40 MPa, advantageously 15 MPa, and the temperature between 0 and 120° C., advantageously 100° C.

Advantageously, stage (2) of the process according to the present invention is carried out in a closed reactor, in particular an autoclave.

The process can be carried out batchwise or continuously. Advantageously, the process according to the present invention is carried out batchwise. Advantageously, stage (2) of the process is carried out in a closed, optionally stirred, reactor fed with the dense fluid and piroxicam, and, if appropriate, continuously.

Carrying out the stage of molecular diffusion in a dense pressurized medium in the presence of a diffusion agent makes possible strong interaction of the piroxicam particles with the cyclodextrins, which promotes the dissolution in an aqueous medium.

The present invention additionally relates to a pharmaceutical composition comprising a piroxicam/cyclodextrin/arginine complex according to the present invention and optionally a pharmaceutically acceptable excipient.

The present invention also relates to a piroxicam/cyclodextrin/arginine complex according to the present invention or a pharmaceutical composition according to the present invention as medicament advantageously having an anti-inflammatory action and advantageously intended to treat inflammatory rheumatism, polyarthritis, arthrosis, tendinitis or post-traumatic conditions of the locomotor apparatus.

The following examples are given by way of indication and without implied limitation.

The various examples provided were carried out with piroxicam as active substance, β-cyclodextrin as host molecule and water as diffusion agent. The aqueous ammonium or arginine was used as agent for interaction with the complex.

DESCRIPTION OF THE FIGURES

FIG. 11 represents the side view with the hydrogen atoms, FIG. 12 represents the side view without the hydrogen atoms, FIG. 13 represents the view of the cavity on the benzothiazine ring side with the hydrogen atoms, FIG. 14 represents the view of the cavity on the benzothiazine ring side without the hydrogen atoms, FIG. 15 represents the view of the cavity on the pyridine ring side with the hydrogen atoms and FIG. 16 represents the view of the cavity on the pyridine ring side without the hydrogen atoms.

ANALYSIS

Figure 1:
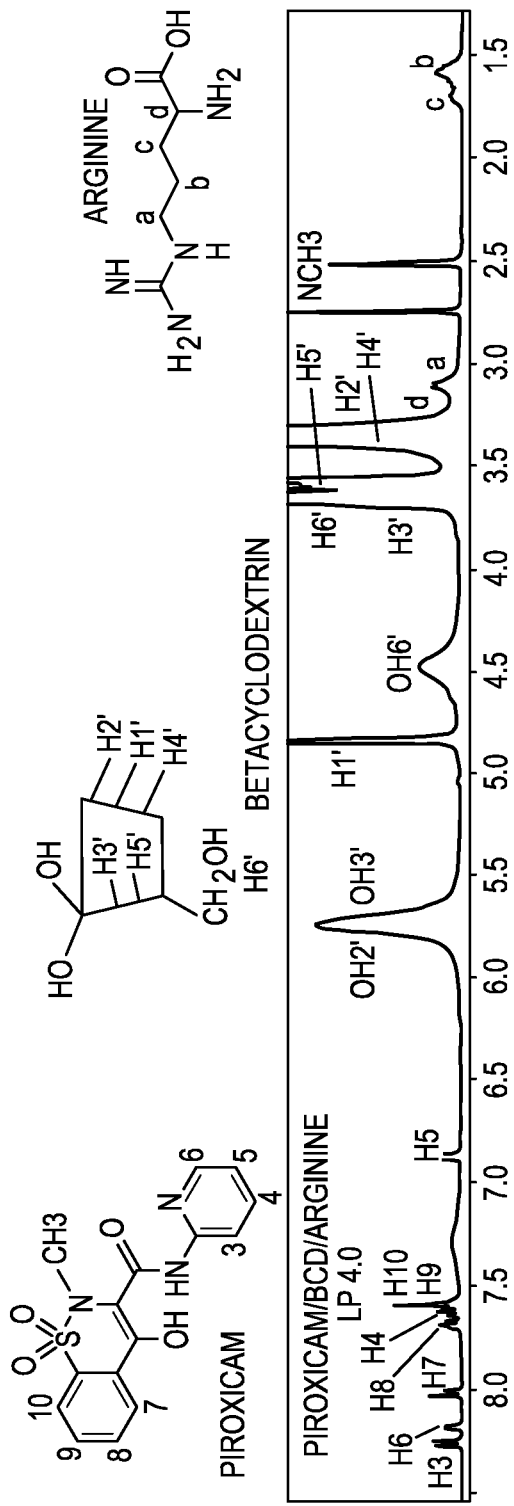
FIG. 1 represents the NMR spectrum of the complex obtained according to example 7.

The degree of inclusion of the active substance in the host molecule is evaluated by differential scanning calorimetry (DSC).

The DSC analyses of the complexes obtained according to examples 1 to 6 were carried out in the following way:

A temperature gradient is applied to the product to be tested under a nitrogen stream using a Perkin-Elmer DSC 7 device.

The complexing efficiency is evaluated by measuring the reduction in (or disappearance of) the thermal peak relative to the melting of the active principle which has "remained free" in the crystalline form.

The DSC analysis of the complex obtained according to example 7 was carried out in the following way:

The equipment, DSC Q100 TA Instruments, was calibrated using the indium melting signal under a stream of nitrogen of 50 ml·min$^{-1}$. The sample is analyzed in a hermetically sealed boat of 5° C.min$^{-1}$.

The thermogravimetric analyses are carried out using the TA Instruments TGA2950 HR equipment in order to determine the thermal stability range of the samples. The device is calibrated at ambient temperature and using the Curie point of nickel at 360.46° C. The accuracy of the balance is confirmed by the analysis of a calcium oxalate sample.

The analysis is carried out under a stream of nitrogen of 60 ml·min$^{-1}$ from 25° C. to 450° C.

The amount of water in the samples is determined by coulometry using the Mettler KF DL37 coulometer. The equipment is calibrated with the sodium tartrate dihydrate standard (% $H_2O$=15.66±0.05%).

Powder X-ray diffraction is carried out with the following equipment and conditions:
Philips Xpert MPD diffractometer, Philips generator, voltage 40 kV, current strength 20 mA.
copper anticathode ($K_\alpha$=1.5418367 angstrom), Ni filter
⅛ entry slit
Xcelerator detector
continuous scan mode
sample ground to a powder on a plate
angular range (° 2θ) 4 to 100
scan time: 80 seconds
Phase analysis is carried out using Visual CRYSTAL software.

The Raman scattering spectra are obtained with the following equipment and conditions:
Jobin Yvon LabRAM HR 800 Raman spectrometer
Temperature: 22° C.
Samples: powder on microscope coverglass
Exciting wavelength: 752 nm, laser power 10 mW on the sample
Spectral resolution 2 cm$^-$, scattering volume approximately 1 μm$^3$ (grating 600 lines)

The proton NMR spectrum is recorded on a Bruker Avance DPX spectrometer at the nominal frequency of 400 MHz using a broad band inverse probe equipped with a field gradient accessory along the Z axis. The spectrometer is locked beforehand on the resonance frequency of the deuterium of the dissolution solvent, in this case $d_6$-dimethyl sulphoxide (Eurisotop, ref. D 310B, batch A 2731). The chemical shifts are given in ppm with respect to TMS (tetramethylsilane), used as internal standard.

The ROESY (Rotating frame Overhauser Enhancement SpectroscopY) spectrum is obtained by applying the Bruker pulse microprogram "roesytp.2".

Recording is carried out in phase-sensitive mode with 1024 increments and 72 scans per increment, i.e. a total experimental time of 53 hours per product. Acquisition is carried out by selecting a spectral window of 6410.256 Hz, a relaxation time of 2 s and a spin lock time of 350 ms. Prior to the recording of the spectrum, the sample is correctly degassed in order to observe the maximum intra- and intermolecular NOE effect.

Due to the low solubility of the complexes in water and to the sensitivity of the NMR spectrometer in our possession, we preferred to work in deuterated dimethyl sulphoxide, in which it is possible to expect a concentration of complex of 2% (w/v).

Molecular modeling: the optimizing of the piroxicam/β-cyclodextrin (1:2) inclusion complex is carried out with Hyperchem®, version 6.02, software (Hypercube, Gainsville, USA), implemented on an HP Vectra model Pentium III personal computer.

The molecular structure of the piroxicam used for the minimization calculations is taken from the publication by Jon Bordner et al. (*Acta Cryst.*, 1984, C40, 989-990).

The molecular structure of the β-cyclodextrin originates from the Cambridge Crystallographic Database (M. R. Caira et al., *J. Chem. Soc., Chem. Commun.*, 1994, 1061-1062).

The energy minimization of the geometry and of the conformation of the complex is carried out using the MM2 force field.

The simulation of the physicochemical propeties (pKa, log D and solubility) from the piroxicam molecule is carried out with the ACD/Log D Suite software (ACD/Labs software, Toronto, Canada).

In order to measure the dissolution properties of the powder, the equivalent of 4 g/l of piroxicam is dissolved in an aqueous solution at 37° C. After 15 min, a sample is taken and then the amount of piroxicam dissolved is measured by HPLC. The result is expressed in grams of piroxicam dissolved per liter of water. According to this method, the solubility of pure piroxicam in water is less than 0.2 g/l.

Piroxicam Dissolution Test

Procedure:

The assaying of piroxicam in the dissolution solution is carried out by HPLC:

Equipment Used:

Waters HPLC System:
  2695 separation module,
  2487 UV detector.

Chromatographic Conditions:
  Column: Waters X-Terra MS C18 250×4.6 mm.
  1.1.1.1.1.1 Mobile Phase: Route A
  60% buffer pH=3.5 $KH_2PO_4$ 6.81 g/l adjusted to the pH with $H_3PO_4$ diluted R,
  40% acetonitrile.
  Flow rate: 1 ml/min
  Detector wavelength: 230 nm
  Sensitivity of the detector: 2 AUFS
  Volume injected: 20 μl
  Oven temperature: 40° C.
  Analysis time: 12 minutes Preparation of the Control Solutions:

Control solution: SM: 50 mg of control piroxicam are introduced into a 100 ml flask. Dissolution is carried out with 20 ml of dimethylformamide and the solution is made up to volume with methanol.

Range:
  T1: Dilution of T3 to $1/20^{th}$ in 40 acetonitrile/60 water.
  T2: Dilution of T3 to $1/10^{th}$ in 40 acetonitrile/60 water.
  T3: Dilution of SM to $1/100^{th}$ in 40 acetonitrile/60 water.
  T4: Dilution of SM to $1/50^{th}$ in 40 acetonitrile/60 water.
  T5: Dilution of SM to $1/20^{th}$ in 40 acetonitrile/60 water.

Operating Conditions for the Kinetics of Dissolution at 4 g/l:

Implementation of the Test:

Operating Conditions:

A test sample equivalent to 200 mg of piroxicam is introduced into a 100 ml Erlenmeyer flask. 50 ml of water are added. The mixture is stirred magnetically at 400 revolutions per minute in a bath thermostatically controlled at 37° C.+/−2° C. A 2 ml sample is withdrawn at 5, 30, 60 and 120 minutes while stirring magnetically. The widthdrawn samples are filtered through a 0.45 μm Gelman GHP Acrodisc polypropylene filter. The solution must be clear. The withdrawn sample is diluted to $1/200^{th}$ in the mobile phase.

Methodology, Expression of the Results:

20 μl of each control solution are injected.

A linear regression is carried out on the areas of the piroxicam peaks with respect to the concentrations. The correlation coefficient must be greater than 0.995.

20 μl of the solutions to be examined are injected.

The area of the peak of piroxicam in each solution to be examined is measured.

The concentration X in μg/ml is deduced therefrom using the regression straight line of the controls.

The concentration of dissolved piroxicam in μg per ml is calculated by multiplying by the inverse of the dilution carried out (i.e.: 200).

The degree of dissolution of the piroxicam is calculated by dividing the concentration of dissolved piroxicam by the total concentration of piroxicam in the starting solution.

Example 1

Results Obtained Using the Process According to the Present Invention 8 grams of piroxicam, 76 grams of β-cyclodextrin and 25.2 g of water are mixed and introduced into a two liter reactor. Carbon dioxide is subsequently introduced into the reactor under a pressure of 200 bar and under a temperature of 150° C. These operating conditions are maintained for a time of two hours.

After the "maturing" stage, a portion of the powder collected (12 g) is mixed with 2.11 g of a 28% ammoniacal solution and then placed in a ventilated oven at 60° C. overnight.

The DSC analysis reveals a degree of inclusion of the piroxicam in the cyclodextrin of 99%; the dissolution of the piroxicam is 3.019 g/l.

Comparative Example 2

Results Obtained after the Maturing Stage without Addition of Agent for Interaction with the Complex 4 grams of piroxicam, 38 grams of β-cyclodextrin and 8.95 grams of water are mixed and introduced into a two liter reactor. Carbon dioxide is subsequently introduced into the reactor under a pressure of 150 bar and under a temperature of 150° C. These operating conditions are maintained for a time of two hours.

After reducing the medium in pressure, a portion of the powder collected is placed in a ventilated oven at 60° C. overnight. The DSC analysis reveals a degree of inclusion of the piroxicam in the cyclodextrin of 80%; the dissolution of the piroxicam is 0.246 g/l.

Comparative Example 3

Results Obtained if the Agent for Interaction with the Complex is Present During the Maturing Stage (b)

2 g of piroxicam, 19 g of β-cyclodextrin, 3.75 g of water and 1.5 g of 28% ammoniacal solution are mixed and introduced into a two liter reactor. Carbon dioxide is subsequently introduced into the reactor under a pressure of 200 bar and under a temperature of 160° C. These operating conditions are maintained for a time of two hours.

After reducing the medium in pressure, the powder collected is placed in a ventilated oven at 60° C. overnight. The DSC analysis reveals a degree of inclusion of the piroxicam in the cyclodextrin of 50%; the dissolution of the piroxicam is 1.075 g/l.

Comparative Example 4

Results Obtained if an Attempt is Made to Attach the Agent for Interaction to the Host Molecule Before the Maturing Stage (b)

19 g of β-cyclodextrin, 2.11 g of 28% ammoniacal solution and 3.15 g of purified water are mixed and placed in a ventilated oven at 60° C. overnight. 2 g of piroxicam and 6.57 g of water are subsequently added. The mixture is subsequently introduced into a two liter reactor. Carbon dioxide is subsequently introduced into the reactor under a pressure of 200 bar and under a temperature of 160° C. These operating conditions are maintained for a time of two hours.

The DSC analysis reveals a degree of inclusion of the piroxicam in the cyclodextrin of 92%; the dissolution of the piroxicam is 0.23 g/l.

Comparative Example 5

Results Obtained if an Attempt is Made to Attach the Agent for Interaction to the Active Substance Before the Maturing Stage (b)

2 g of piroxicam and 2 g of 28% ammoniacal solution are mixed and placed in a ventilated oven at 60° C. overnight. 14.3 g of β-cyclodextrin and 3.3 g of water are subsequently added. The mixture is subsequently introduced into a two liter reactor. Carbon dioxide is subsequently introduced into the reactor under a pressure of 150 bar and under a temperature of 150° C. These operating conditions are maintained for a period of two hours.

The DSC analysis reveals a degree of inclusion of the piroxicam in the cyclodextrin of 56%; the dissolution of the piroxicam is 1.370 g/l.

Example 6

Results Using the Process According to the Present Invention on Batches of Semi-Industrial Size: 12.5 kg 1.1 kg of piroxicam, 10.6 kg of β-cyclodextrin and 1.3 kg of water are mixed and introduced into a 50 liter reactor. Carbon dioxide is subsequently introduced into the reactor under a pressure of 150 bar and under a temperature of 100° C. These operating conditions are maintained for a time of two hours.

A portion of the powder is placed in an oven at 80° C. overnight.

The DSC analysis reveals a degree of inclusion of the piroxicam in the cyclodextrin of 89%; the dissolution of the piroxicam is 1.937 g/l.

The powder collected (12.6 kg) is mixed with 2.6 kg of a 28% ammoniacal solution and then placed in a ventilated oven at 60° C.

The DSC analysis reveals a degree of inclusion of the piroxicam in the cyclodextrin of 100%; the dissolution of the piroxicam is greater than 3 g/l.

Summary of the Results Obtained

Table 1 below collates the results of the various examples 1 to 6 indicated above and makes it possible to observe the added value of the process according to the present invention.

TABLE 1

| Process/Materials | / | Ex. 1 | Comp. Ex. 2 | Comp. Ex. 3 | Comp. Ex. 4 | Comp. Ex. 5 | Ex. 6 |
|---|---|---|---|---|---|---|---|
| Materials involved: | | | | | | | |
| Piroxicam | X | X | X | X | X | | X |
| Piroxicam mixed beforehand with the agent for interaction with the complex | | | | | | X | |
| β-Cyclodextrin | | X | X | X | | X | X |
| β-Cyclodextrin mixed beforehand with the agent for interaction with the complex | | | | | X | | |
| 1st phase: Complexing in supercritical $CO_2$ medium | | X | X | | X | X | X |
| 2nd phase: Addition of the agent for interaction with the complex | | X | | | | | X |
| 1 single phase: Complexing with the agent for interaction with the complex in supercritical $CO_2$ medium | | | | X | | | |

TABLE 1-continued

| Process/Materials | / | Ex. 1 | Comp. Ex. 2 | Comp. Ex. 3 | Comp. Ex. 4 | Comp. Ex. 5 | Ex. 6 |
|---|---|---|---|---|---|---|---|
| Degree of complexing (DSC) | / | 99% | 80% | 50% | 92% | 56% | 100% |
| Dissolution (g/l) | <0.2 | 3.02 | 0.25 | 1.07 | 0.23 | 1.37 | >3 |

Example 7

Piroxicam/β-Cyclodextrin/Arginine Complex 43 grams of piroxicam, 384 grams of β-cyclodextrin and 25 grams of arginine are introduced into a reactor, along with 61 grams of diffusion agent (water). Carbon dioxide is subsequently introduced into the reactor under a pressure of 15 MPa and under a temperature of 100° C. These operating conditions are maintained for a time of one hour.

The kinetics of dissolution and the degree of dissolution are measured on the complexes obtained as indicated above in the "PIROXICAM dissolution test". The results are collated in table 2 below.

| Time (minutes) | Piroxicam concentration (μg/ml) | Degree of dissolution (%) |
|---|---|---|
| 5 | 3863 | 96.6 |
| 30 | 3854 | 96.4 |
| 60 | 3941 | 98.5 |
| 120 | 3962 | 99 |

NMR:

The $^1$H NMR spectrum of a complex obtained according to example 7 (FIG. 1) is in agreement with the chemical composition of this compound.

The signal observed at 13.5 ppm is attributed to the pyridinium proton, providing additional proof of the existence of a zwitterionic structure of the piroxicam in the complex obtained according to example 7.

Figure 2:
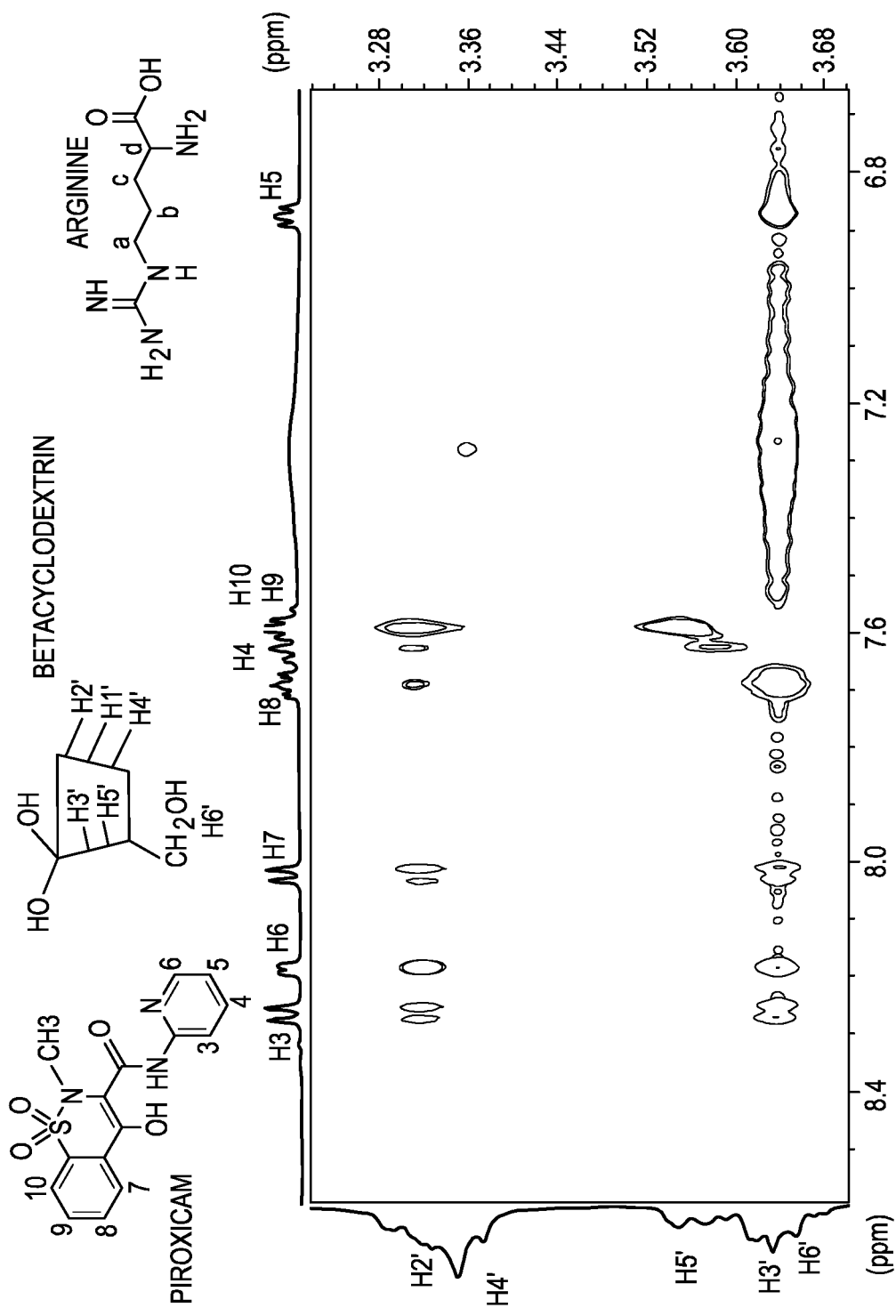
FIG. 2 represents the ROESY-intramolecular NOE spectrum of the complex obtained according to example 7.

Analysis of the ROESY Spectrum (FIG. 2)

This study, which makes it possible to study the transfers of magnetization between protons close in space, will enlighten us on the form of inclusion of the piroxicam in the β-cyclodextrin and will thus allow us to model the corresponding complex.

From the ROESY chart, the intramolecular NOE effects (between protons of the same molecule) are distinguished from the intermolecular NOE effects (between protons belonging to different molecules). While the intramolecular NOE effects are, of course, instructive in terms of conformation analysis, we will mention only the intermolecular NOE effects, which provide evidence of an encapsulation of the piroxicam in the β-cyclodextrin.

The analysis of the ROESY spectrum, recorded on a complex obtained according to example 7 (FIG. 2), clearly shows cross-relaxation peaks between H-9/10 of the piroxicam and H-5' of the βCD and then between H-7, H-6 and H-3 of the piroxicam and H-3' of the β-cyclodextrin. These results are in agreement with a 1:2 piroxicam:β-cyclodextrin inclusion complex.

Figure 3:
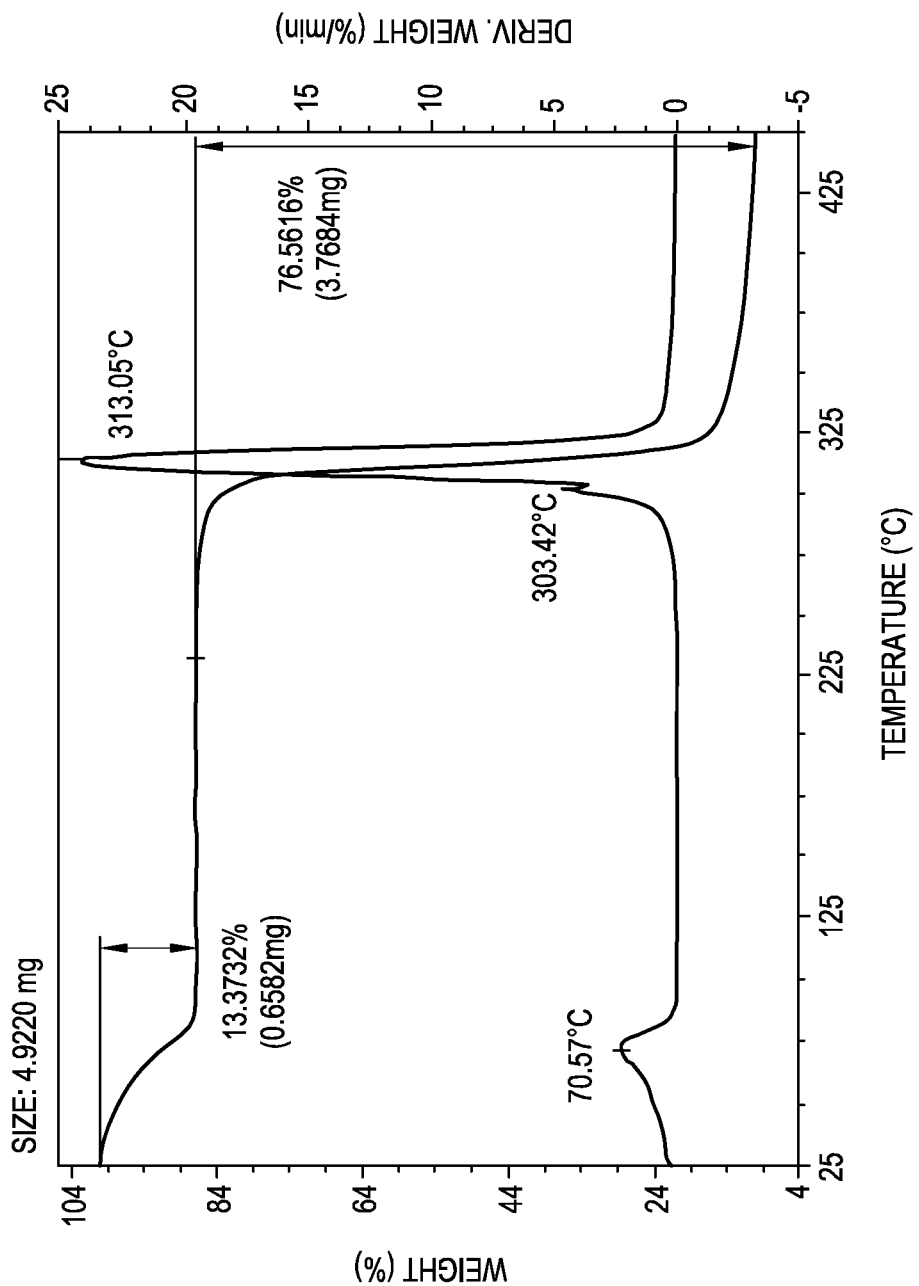
FIG. 3 represents the TG-DTG profile (thermogravimetric analysis) of β-cyclodextrin using the following process: increase in temperature of 5° C. per minute up to 450° C. and then decrease in the temperature of 10° C. per minute down to 80° C.

Thermal Analysis and Assaying of Water:

The thermogravimetric analysis of β-cyclodextrin (FIG. 3) demonstrates two transitions at 70.6° C. and 313° C. The first corresponds to a loss in weight of 13.4%, in agreement with the amount of water determined by coulometry (14.1%), and the second transition is attributed to the thermal decomposition of the β-cyclodextrin.

Figure 4:
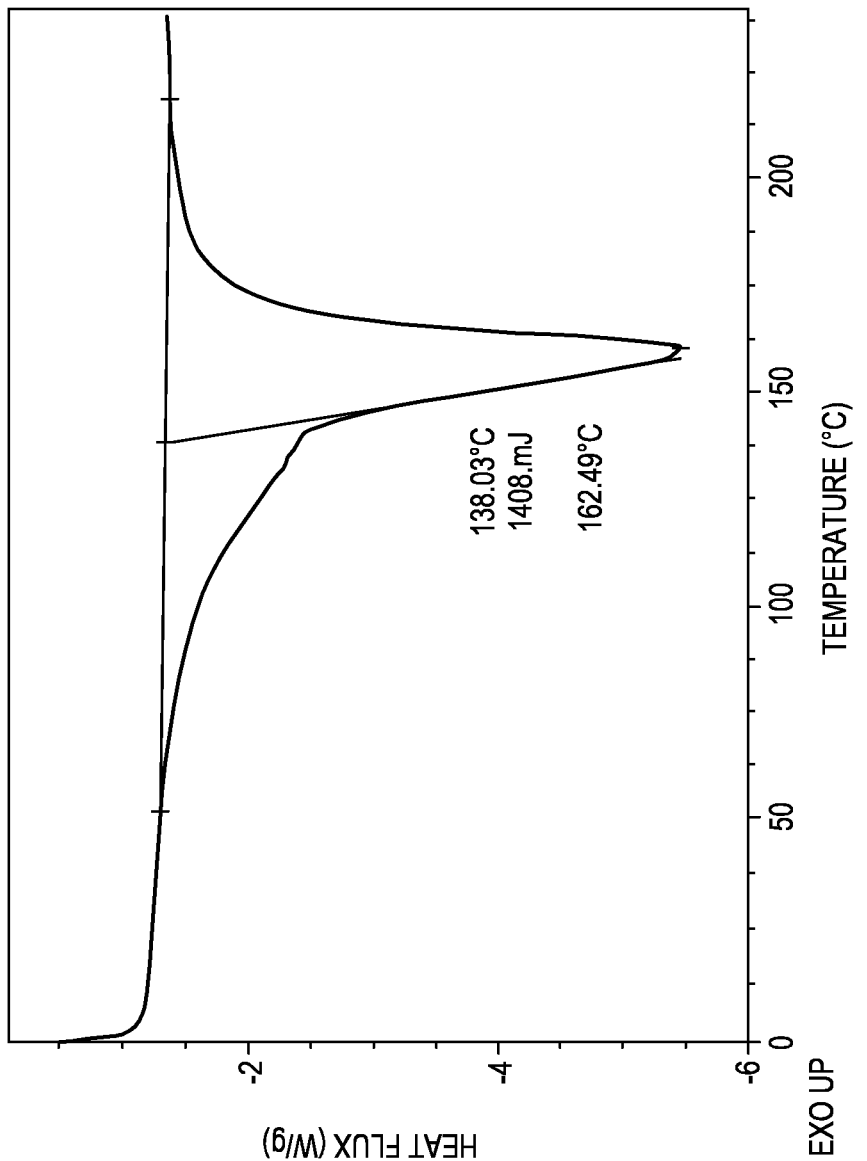
FIG. 4 represents the DSC profile of β-cyclodextrin using the following method: equilibration at 0° C. followed by an increase in the temperature of 5° C. per minute up to 240° C.
Figure 5:
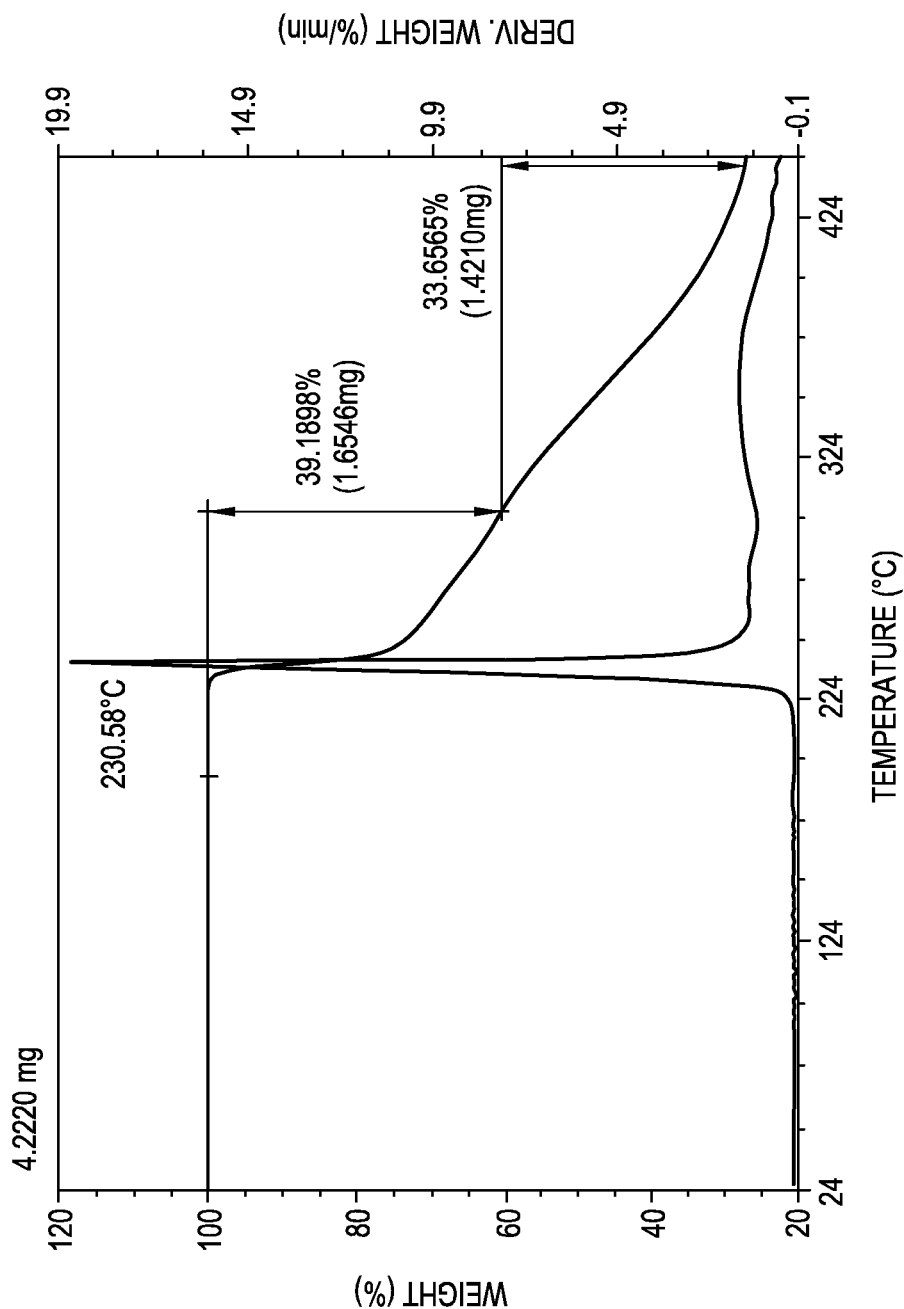
FIG. 5 represents the profile of the thermogravimetric analysis of L-arginine using the same process as that of FIG. 3.
Figure 6:
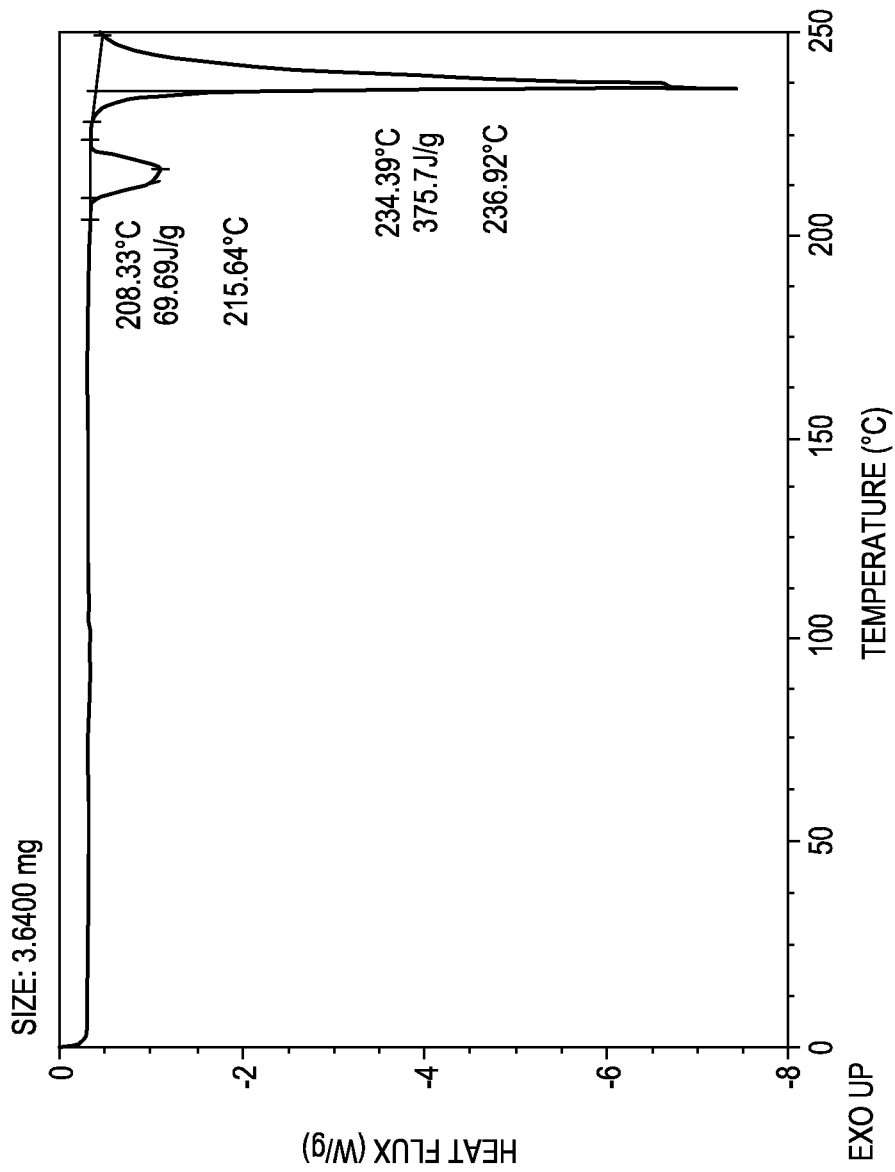
FIG. 6 represents the DSC profile of L-arginine using the same process as that of FIG. 4.

The DSC analysis (FIG. 4) shows a broad endotherm centered on 162° C. corresponding to the dehydration phenomenon. The thermogravimetric analysis of arginine (FIG. 5) shows that the latter is stable up to approximately 230° C. before decomposing. Two endothermy are observed on the DSC profile (FIG. 6), the first at 215.6° C. (melting or phase transition) and the second at 234° C., related to the decomposition phenomenon.

Figure 7:
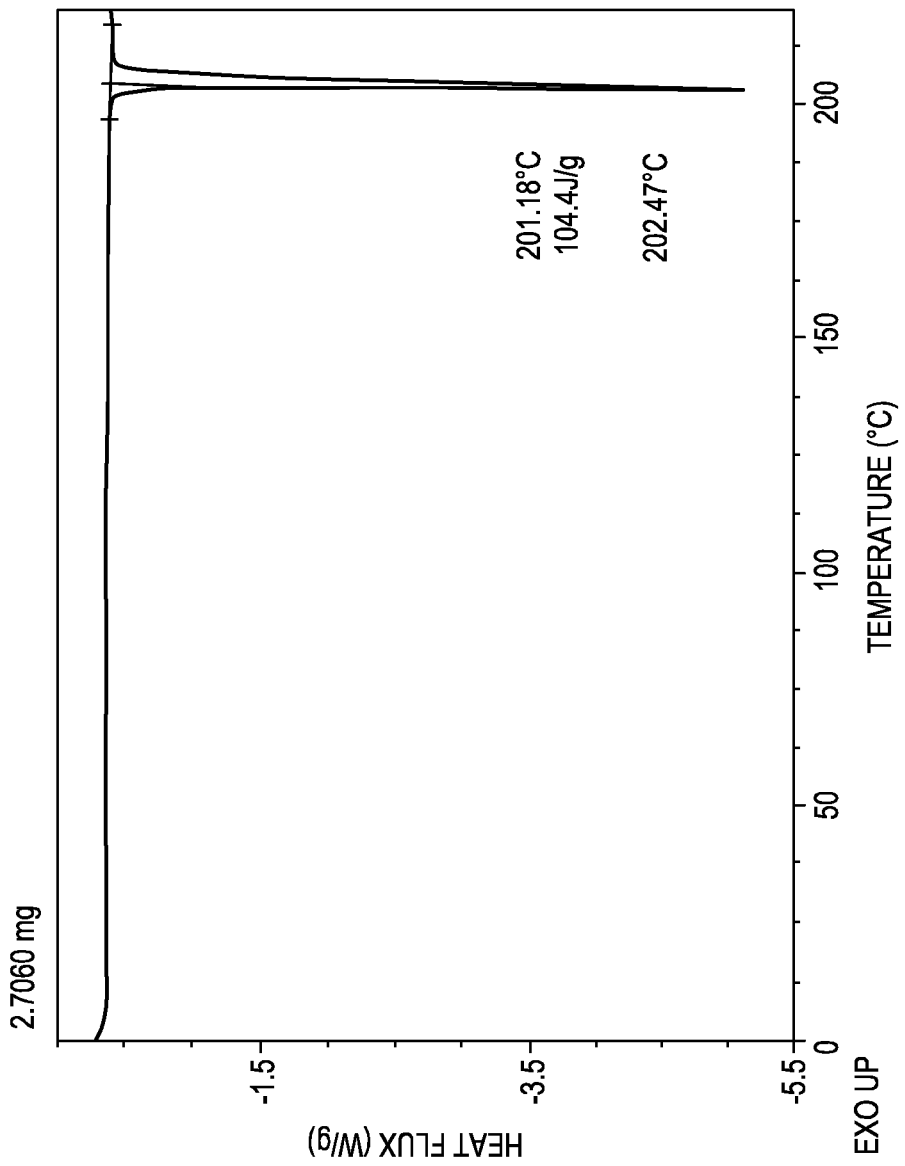
FIG. 7 represents the DSC profile of piroxicam using the same process as that of FIG. 6.

The DSC profile of piroxicam shows that melting occurs at 201° C. with an enthalpy of 104 J·g$^{-1}$ (FIG. 7).

Figure 8:
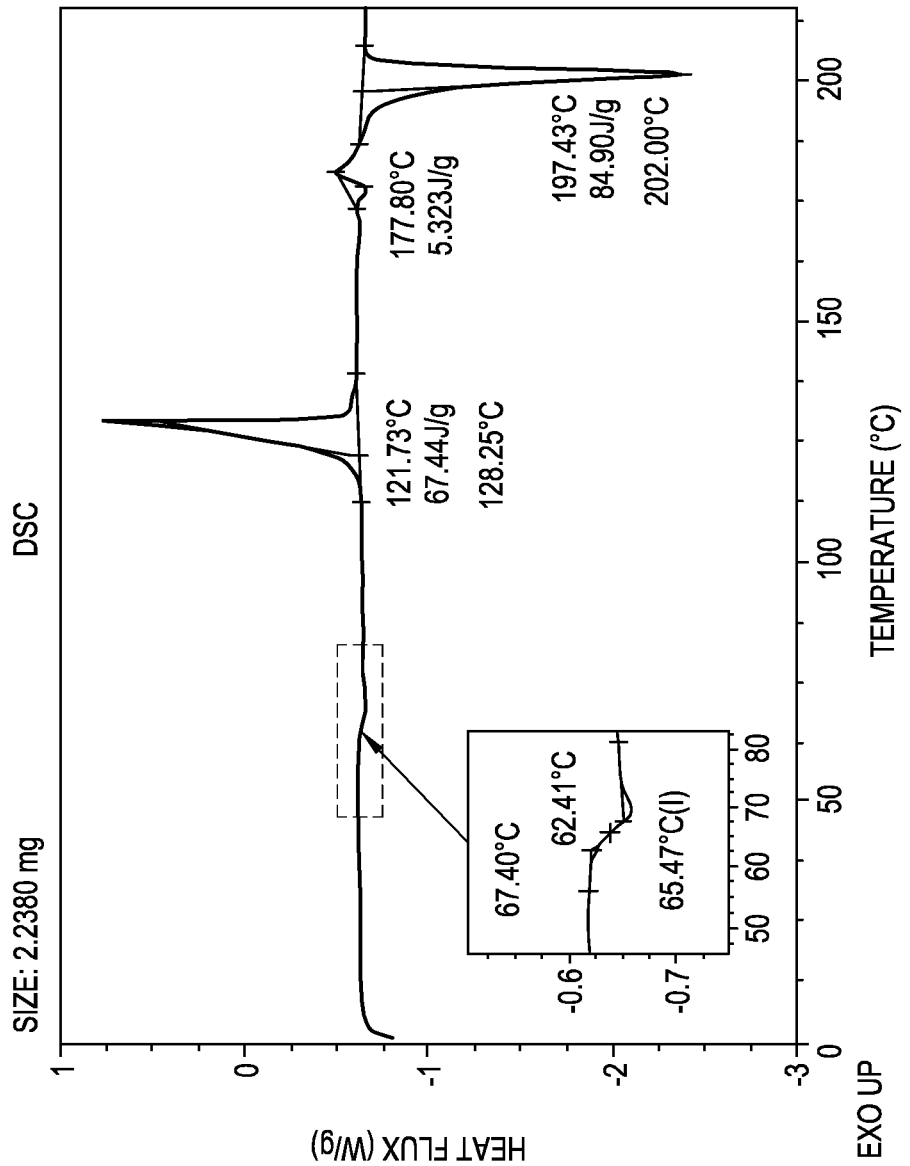
FIG. 8 represents the DSC profile of a sample of piroxicam melted at 260° C. and then cooled to 0° C., using the process of equilibration at 205° C., of decrease in the temperature of 20° C. per minute down to 0° C. and of increase in the temperature of 5° C. per minute up to 220° C.

Heating/cooling cycles are carried out in which a piroxicam sample is melted at 205° C. and then cooled to 0° C. The DSC profile of this sample (FIG. 8) reveals the existence of a glass transition at 62° C., characteristic of the amorphous state, which crystallizes at 122° C. A weak endotherm at 178° C., followed by an exotherm and then by a final endotherm at 197° C. reflects the existence of several crystalline forms of the piroxicam (polymorphism).

The two endothermy at 178° C. and 197° C. would be attributed respectively to the melting of the forms III and II, while the initial sample before the heat treatment would correspond to the form I (melting at 201° C.) (F. Vrečer, S. Srčiči and J. Šmid-Korbar, *International Journal of Pharmaceutics*, 68 (1991), 35-41).

The water content of the complex obtained according to example 7 is of the order of 10% w/w, as indicated in the following table 3:

TABLE 3

Result of the assays of water in the complex of example 7

| Complex | H$_2$O content (TGA) | H$_2$O content (coulometry) |
|---|---|---|
| Obtained according to example 7 | 9.99% | 10.14% |

Figure 9:
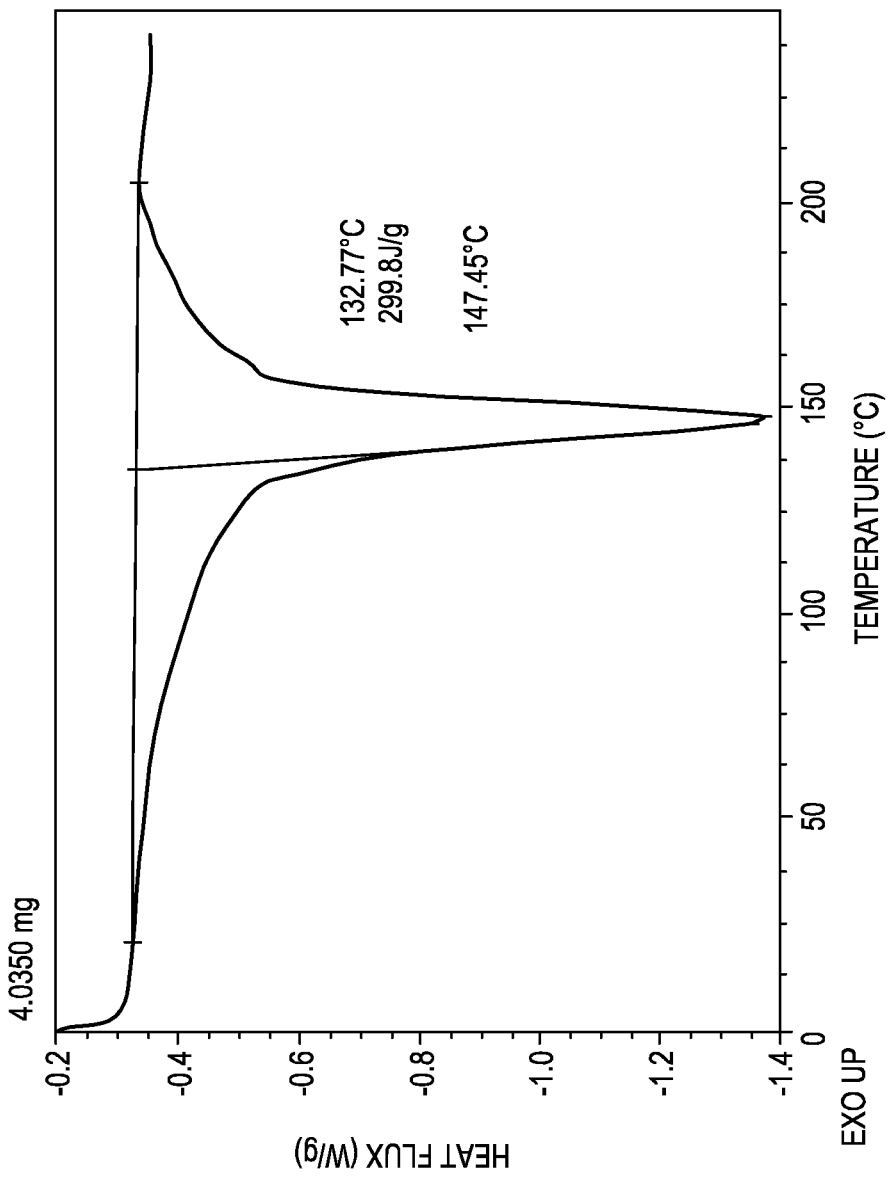
FIG. 9 represents the DSC profile of the complex obtained according to example 7, using the process of equilibration at 0° C., of increase in the temperature of 5° C. per minute up to 240° C. and then of decrease in the temperature of 5° C. per minute down to 80° C.

The DSC profile of the complex obtained according to example 7 (FIG. 9) does not show the transitions at 198-200° C. and at 218° C., suggesting an inclusion of approximately 100%.

Figure 10:
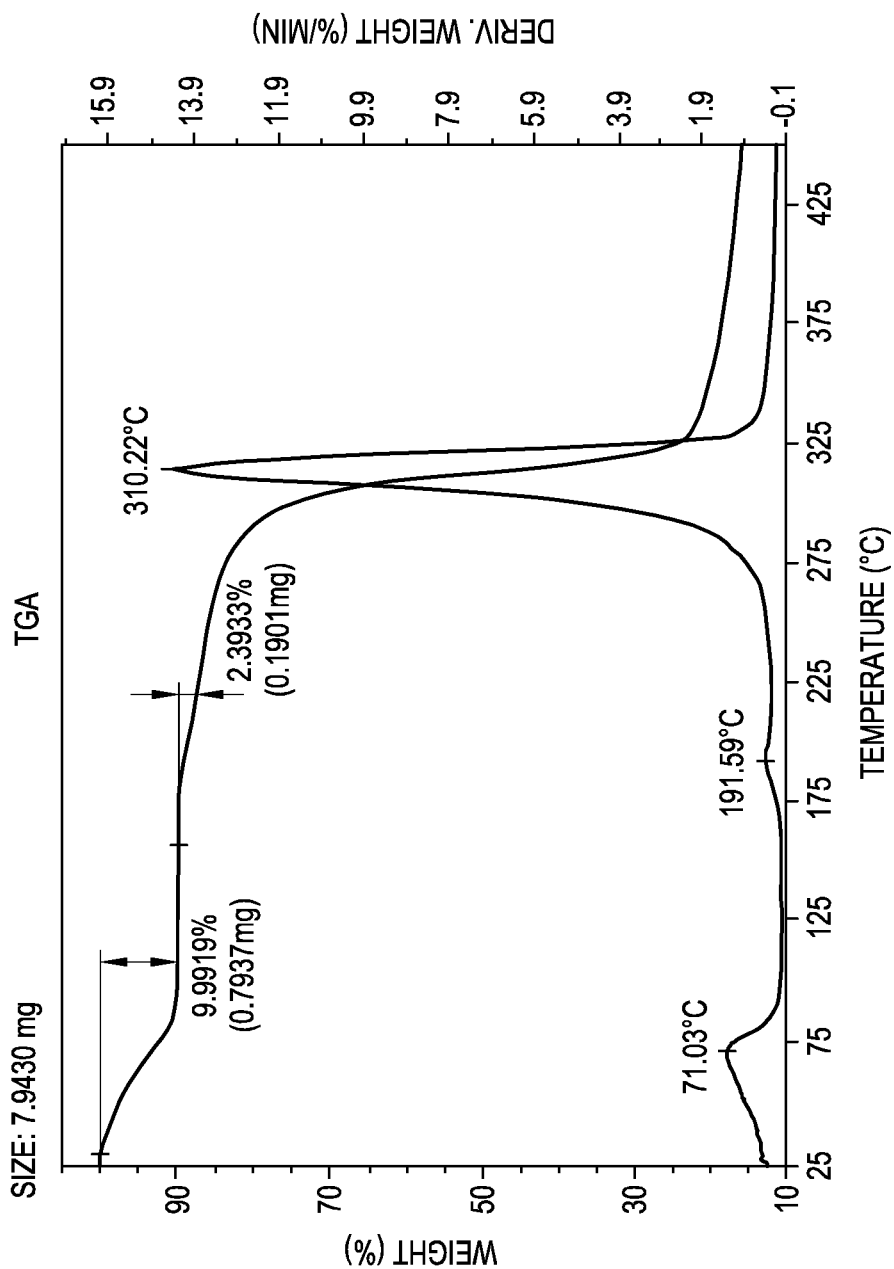
FIG. 10 represents the TG-DTG profile of the complex obtained according to example 7, using the process of increase in the temperature of 5° C. per minute up to 450° C. and then of decrease in the temperature of 10° C. per minute down to 80° C.
Figure 11:
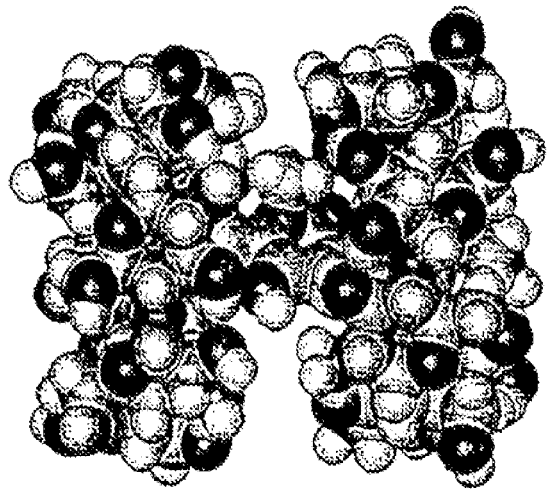
FIGS. 11 to 16 represent the molecular modeling of the minimized structure of the piroxicam/β-cyclodextrin 1:2 inclusion complex. In particular.
Figure 12:
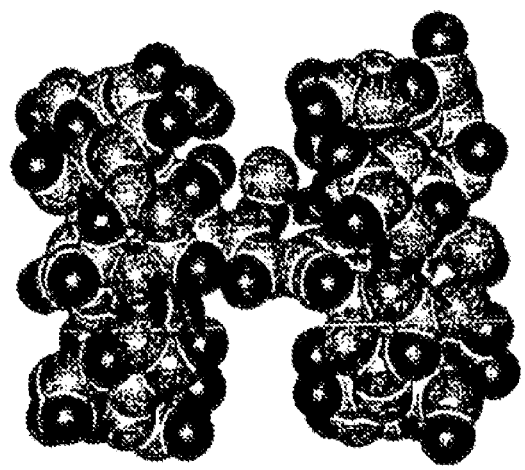
Figure 13:
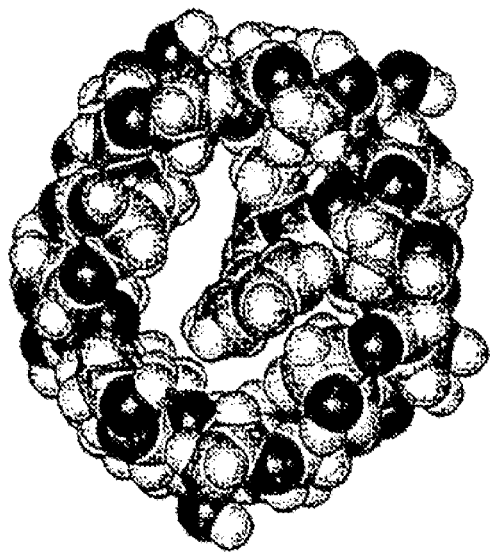
Figure 14:
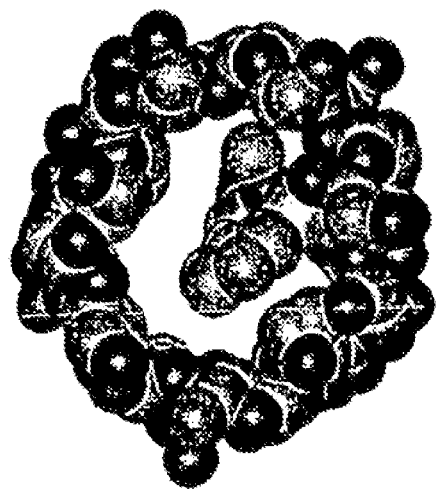
Figure 15:
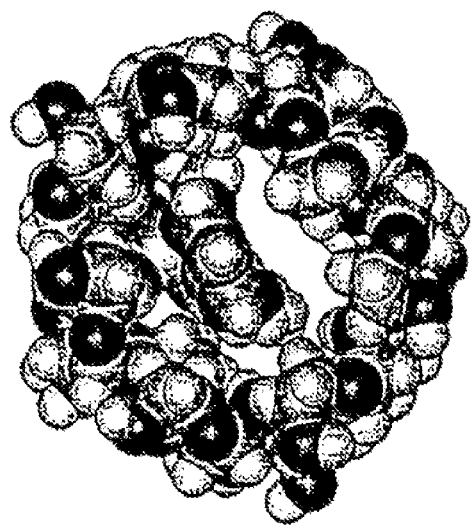
Figure 16:
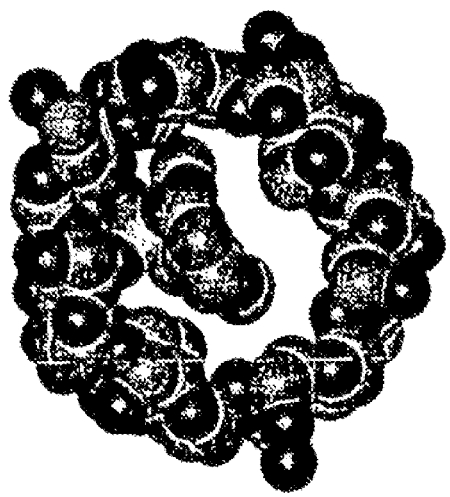

The TG DTG profile of the complex obtained according to example 7 (FIG. 10) shows a transition at 191° C. This transition is attributed to the decomposition of the arginine. This is because the first stage of decomposition of the arginine corresponds to a loss in weight of the order of 39.2% and, if the content of arginine in the complex is taken into account, approximately 6% w/w (determination by NMR), this loss in weight should be of the order of 2.35% w/w, in excellent agreement with that observed on the TG and DTG profiles at 191° C. (2.40%).

Molecular modeling: The minimized structure of the piroxicam:β-cyclodextrin (1:2) inclusion complex is represented in FIGS. 11 to 16. This optimized structure takes into account the spatial interactions observed by ROESY spectrometry.

As is indicated in the publication by G. M. Escandar (*Analyst*, 1999, 124, 587-591), the piroxicam molecule is too bulky (approximately 6×13.7 Å) to be completely encapsulated in a β-cyclodextrin cavity. With a PX:(βCD)$_2$ complex, the piroxicam molecule is completely included.

Figure 17:
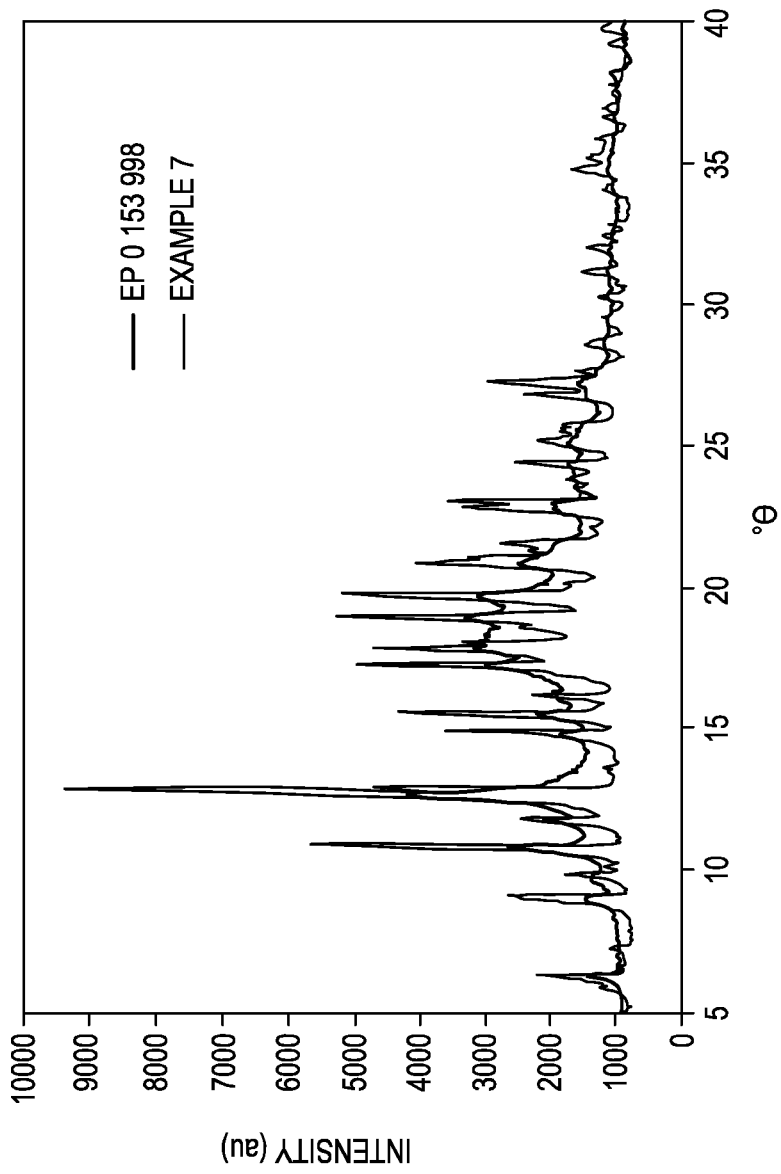
FIG. 17 represents the X-ray diffraction diagram of the complex obtained according to example 7 and of the complex obtained with the process of patent EP 0 153 998.

Simulation of the physicochemical properties: variation in solubility of the piroxicam as a function of the pH of the dissolution medium. The zwitterionic structure presents between pH 2 and 6 the lowest solubility. For its part, the log D value changes in the opposite sense. In the pH range 2-6, the molecule is relatively hydrophobic, which represents another interaction favorable to the encapsulation. Between pH 6 and pH 7.5, the zwitterion is still present and the solubility value increases substantially as a function of the pH, hence the interest in preparing complexes in this pH region in order to combine the two solubilizing effects, which are the encapsulation, on the one hand, and the salification of the piroxicam, on the other hand. The pH values measured are shown below: complex according to example 7 at 13.9 mg/10 ml H$_2$O=pH 7.87. X-ray diffractions of the complex obtained according to example 7 and of the complex obtained according to the process disclosed in EP 0 153 998: the diffraction diagram is represented in FIG. 17. The powder diffraction diagram of the complex according to example 7 shows intense and very well resolved diffraction lines, providing evidence of better crystallinity of this sample in comparison with that of the complex according to the process of patent EP 0 153 998. According to the Visual CRYSTAL software, the complex obtained according to example 7 exhibits between 16 and 20% by weight of amorphous phase.

Example 8

Piroxicam/β-Cyclodextrin/Arginine Complex 400 grams of piroxicam, 3832 grams of β-cyclodextrin and 253 grams of arginine are introduced into a reactor, along with 613 grams of diffusion agent (water). Carbon dioxide is subsequently introduced into the reactor under a pressure of 15 MPa and under a temperature of 100° C. These operating conditions are maintained for a time of one hour.

The kinetics of dissolution and the degree of dissolution are measured on the complexes obtained as indicated above in the "PIROXICAM dissolution test". The results are collated in table 3 below.

| Time (minutes) | Piroxicam concentration (μg/ml) | Degree of dissolution (%) |
|---|---|---|
| 5 | 3953 | 98.8 |
| 30 | 3895 | 97.3 |
| 60 | 3952 | 98.8 |
| 120 | 4041* | 100 |

*Result consistent with the uncertainty related to the measurement.

What is claimed is:

1. A complex comprising piroxicam, a cyclodextrin and arginine, wherein the degree of dissolution of the piroxicam present in a 4 g/l solution in water, measured at 37° C. after stirring at 400 rpm for between 5 and 120 minutes, is greater than 90%.

2. A complex comprising piroxicam, a cyclodextrin and arginine according to claim 1, wherein it comprises less than 40% by weight of amorphous phase.

3. The complex of claim 2, wherein it comprises less than 30% by weight of amorphous phase.

4. The complex as claimed in claim 1, wherein the cyclodextrin is β-cyclodextrin.

5. The complex of claim 1, wherein the degree of dissolution of the piroxicam present in a 4 g/l solution in water, measured at 37° C. after stirring at 400 rpm for between 5 and 120 minutes, is greater than 95%.

6. The complex of claim 1, wherein the degree of dissolution of the piroxicam present in a 4 g/l solution in water, measured at 37° C. after stirring at 400 rpm for between 5 and 120 minutes, is greater than 99%.

7. A pharmaceutical composition comprising a complex as claimed in claim 1 and optionally a pharmaceutically acceptable excipient.

8. A process for the preparation of a complex as claimed in claim 1, wherein it comprises the following successive stages:
   (1) bringing piroxicam into contact with a cyclodextrin and arginine,
   (2) carrying out a stage of molecular diffusion by bringing a dense pressurized fluid into contact, in static mode, with the mixture obtained in stage (1) in the presence of one or more diffusion agents chosen from the group consisting of alcohols, ketones, ethers, esters and water with or without surfactant, and their mixtures,
   (3) recovering the piroxicam/cyclodextrin/arginine complex thus formed.

9. The process as claimed in claim 8, wherein the dense pressurized fluid is carbon dioxide.

10. The process as claimed in claim 8, wherein the diffusion agent is water.

11. The process as claimed in claim 8, wherein stage (2) of molecular diffusion is carried out with stirring.

12. The process as claimed in claim 8, wherein the diffusion agent is added continuously or portionwise in an amount of between 1 and 50% by weight with respect to the total weight of the mixture.

13. The process of claim 8, wherein the diffusion agent is added continuously or portionwise in an amount of between 10 and 25% by weight with respect to the total weight of the mixture.

14. A method for treating an inflammatory disorder comprising the administration of an effective amount of the complex as claimed in claim 1 to a patient in need thereof.

15. The method of claim 14, wherein the inflammatory disorder is inflammatory rheumatism, polyarthritis, arthrosis, tendinitis or post-traumatic conditions of the locomotor apparatus.

* * * * *